United States Patent [19]
Thompson et al.

[11] Patent Number: 6,150,043
[45] Date of Patent: Nov. 21, 2000

[54] OLEDS CONTAINING THERMALLY STABLE GLASSY ORGANIC HOLE TRANSPORTING MATERIALS

[75] Inventors: Mark E. Thompson, Anaheim; Loy Douglas, Lakewood, both of Calif.; Diarmuid O'Brien, Princeton, N.J.; Bryan E. Koene, South Pasadena, Calif.; Stephen R. Forrest, Princeton, N.J.

[73] Assignees: The Trustees of Princeton University, Princeton, N.J.; The University of Southern California, Los Angeles, Calif.

[21] Appl. No.: 09/058,305

[22] Filed: Apr. 10, 1998

[51] Int. Cl.⁷ .............................. B32B 19/04; H01J 1/63; C07D 223/14

[52] U.S. Cl. ..................... 428/690; 428/917; 313/504; 313/506; 540/543

[58] Field of Search ...................... 252/307.17; 428/917, 428/690; 540/543; 313/504, 506

[56] References Cited

U.S. PATENT DOCUMENTS

| | | |
|---|---|---|
| 4,769,292 | 9/1988 | Tang et al. . |
| 5,061,569 | 10/1991 | VanSlyke et al. . |
| 5,294,869 | 3/1994 | Tang et al. . |
| 5,294,870 | 3/1994 | Tang et al. . |
| 5,409,783 | 4/1995 | Tang et al. . |
| 5,457,565 | 10/1995 | Namiki et al. . |
| 5,554,220 | 9/1996 | Forrest et al. . |
| 5,703,436 | 12/1997 | Forrest et al. . |
| 5,707,745 | 1/1998 | Forrest et al. . |

FOREIGN PATENT DOCUMENTS

10-219241  8/1998  Japan .

OTHER PUBLICATIONS

Berggren, M., et al., Light Amplification in Organic Thin Films Using Cascade Energy Transfer, *Nature* 389, 466 (1997).

Kalinowski, J., et al., "Electroabsorption Study of Excited States in Hydrogen–bonding Solids: Epindolidone and Linear Trans–quinacridone," *Chem. Phys.* 182, 341 (1994).

D. Kim, et al., "Synthesis of Electroluminescent Polymer Containing Charge Transport and Emissive Chromophores on Polymer Skeleton", *Chemistry Letters*, pp. 587–588, (1995).

Kim, H.H., et al., "Silicon Compatible Organic Light Emitting Diode", *Journal of Lightwave Technology*, vol. 12, No. 12, pp. 2107–2113 (Dec. 1994).

Martin, M., et al., "Ultrafast Intramolecular Charge Transfer in the Merocyanine Dye DCM," *Chem. Phys.* 192, 367 (1995).

N. Tamoto, et al., "Electroluminescence of 1,3,4–Oxadiazole and Triphenylamine–Containing Molecules as an Emitter in Organic Multilayer Light Emitting Diodes", *Chem. Mater.*, (1997), vol. 9, No. 5, 1077–1085.

Tang, C.W., et al., "Electroluminescence of Doped Organic Thin Films," *J. Appl. Phys.* 65,3610 (1989).

Co–pending U.S. Application of Thompson, M.E. et al, "OLEDs Containing Thermally Stable Asymmetric Charge Carrier Materials", Serial No. 08/929,029 filed Sep. 8, 1997.

Bulovic et al., "Transparent Light–emitting Devices", *Nature* 380, 29 (1996).

Whitlock et al., "Investigations of Materials and Device Structures for Organic Semiconductor Solar Cells", *Optical Eng.*, vol. 32., No. 8, 1921–1934 (Aug. 1993).

(List continued on next page.)

*Primary Examiner*—Floyd D. Higel
*Assistant Examiner*—Ebenezer Sackey
*Attorney, Agent, or Firm*—Kenyon & Kenyon

[57] ABSTRACT

The present invention is directed to organic light emitting devices comprising a heterostructure for producing electroluminescence having a hole transporting layer with a glass structure. The hole transporting layer comprises a compound having a symmetric molecular structure. The end groups of the symmetric molecule are hole transporting amine moieties having an unsaturated linkage between two arenes.

22 Claims, 2 Drawing Sheets

OTHER PUBLICATIONS

Forrest, S.R., et al., "Organic Emitters Promise a New Generation of Displays," *Laser Focus World*, Feb. 1995, pp. 99–107.

Han, E., et al., "Scanning Force Microscopy of Organic Thin–Film Amorphous Hole Transport Materials," *J. Appl. Phys.*, vol. 80, 1996, pp. 3297–3305.

Inada, H., et al., "Photo– and Electro–active Amorphous Molecular Materials: Morphology, Structures, and Hole Transport Properties of Tri(biphenyl–4–yl)amine," *J. Mater. Chem.*, 1994, vol. 4, 1994, pp. 171–177.

Naito, K., et al., "Molecular Design for Nonpolymeric Organic Dye Glasses with Thermal Stability: Relations Between Thermodynamic Parameters and Amorphous Properties," *J. Phys. Chem.*, vol. 97, 1993, pp. 6240–6248.

Noda, T., et al., "A Novel Yellow–emitting Material, 5,5"–bis{4–[bis(4–methylphenyl)amino]phenyl}–2,2':5',2"–Terthiophene, for Organic Electroluminescent Devices," *Appl. Phys. Lett.*, vol. 70, No. 6, 1997, pp. 699–701.

Noda, T., et al., "5,5"–Bis{4–methylphenyl)amino]phenyl}–2,2':5',2"–Terthiophene and . . . as a Novel Family of Amorphous Molecular Materials," *Advance Materials*, vol. 9, No. 3, 1997, pp. 239–241.

Rommens, J., et al., "Hole Injection into Molecular Dispersions of 5'–[4–[Bis(4–ethylphenyl)amino]phenyl]–. . . –terphenyl]–4,4"–diamine," *American Chemical Society*, vol. 101, No. 16, 1997, pp. 3081–3086.

Salbeck, J., et al., "Low Molecular Organic Glasses for Blue Electroluminescence," *Synthetic Metals*, vol. 91, 1997, pp. 209–215.

Shirota, Y., et al., "Starburst Molecules for Amorphous Molecular Materials . . . N–phenylamino]triphenylamine," *Chem. Lett.*, 1989, pp. 1145–1148.

Tang, C.W., et al., "Organic Electroluminescent Diodes," *Appl. Phys. Lett.*, vol. 51, No. 12, Sep. 1987, pp. 913–915.

Tokito, S., et al., "High–Temperature Operation of an Electroluminescent Device Fabricated Using a Novel Triphenylamine Derivative," *Appl. Phys. Lett.*, vol. 69, No. 7, 1996, pp. 878–880.

Van Slyke, S.A., et al., "Organic Electroluminescent Devices with Improved Stability," *Appl. Phys. Lett.*, vol. 69, No. 15, 1996, pp. 2160–2162.

Copending U.S. application No. 08/865,491, "An Organic Light Emitting Device Containing a Hole Injection Enhancement Layer," filed May 29, 1997.

Copending U.S. application No. 08/964,863, "A Highly Transparent Organic Light Emitting Device Employing a Non–Metallic Cathode," filed Nov. 5, 1997.

Copending U.S. application No. 09/054,707, "Highly Transparent Non–Metallic Cathodes," filed Apr. 3, 1998.

Copending U.S. application No. 08/925,029, "OLEDs Containing Thermally Stable Asymmetric Charge Carrier Materials," filed Sep. 8, 1997.

OLEDS CONTAINING THERMALLY STABLE GLASSY ORGANIC HOLE TRANSPORTING MATERIALS

GOVERNMENT RIGHTS

This invention was made with Government support under Contract No. F33615-94-1-1414 awarded by DAPRA. The government has certain rights in this invention.

FIELD OF INVENTION

The present invention is directed to organic light emitting devices (OLEDs) comprised of glassy organic hole transporting materials comprised of compounds having a symmetric molecular structure, for example, hole transporting materials comprised of thermally stable symmetric derivatives of phenyl or biphenyl diamines.

BACKGROUND OF THE INVENTION

Organic light emitting devices (OLEDs) are comprised of several organic layers in which one of the layers is comprised of an organic material that can be made to electroluminesce by applying a voltage across the device. C. W. Tang et al., *Appl. Phys. Lett.* 51, 913 (1987). Certain OLEDs have been shown to have sufficient brightness, range of color and operating lifetimes for use as a practical alternative technology to LCD-based full color flat-panel displays. S. R. Forrest, P. E. Burrows and M. E. Thompson, Laser Focus World, February 1995. Since many of the thin organic films used in such devices are transparent in the visible spectral region, they allow for the realization of a completely new type of display pixel in which red (R), green (G), and blue (B) emitting OLEDs are placed in a vertically stacked geometry to provide a simple fabrication process, a small R-G-B pixel size, and a large fill factor.

A transparent OLED (TOLED), which represents a significant step toward realizing high resolution, independently addressable stacked R-G-B pixels, was reported in U.S. Pat. No. 5,703,436, Forrest et al. This TOLED had greater than 71% transparency when turned off and emitted light from both top and bottom device surfaces with high efficiency (approaching 1% quantum efficiency) when the device was turned on. The TOLED used transparent indium tin oxide (ITO) as the hole-injecting electrode and a Mg—Ag—ITO electrode layer for electron-injection. A device was disclosed in which the ITO side of the Mg—Ag—ITO electrode layer was used as a hole-injecting contact for a second, different color-emitting OLED stacked on top of the TOLED. Each layer in the stacked OLED (SOLED) was independently addressable and emitted its own characteristic color, red or blue. This colored emission could be transmitted through the adjacently stacked transparent, independently addressable, organic layer, the transparent contacts and the glass substrate, thus allowing the device to emit any color that could be produced by varying the relative output of the red and blue color-emitting layers.

U.S. Pat. No. 5,703,745, Forrest et al, disclosed an integrated SOLED for which both intensity and color could be independently varied and controlled with external power supplies in a color tunable display device. U.S. Pat. No. 5,703,745, thus, illustrates a principle for achieving integrated, full color pixels that provide high image resolution, which is made possible by the compact pixel size. Furthermore, relatively low cost fabrication techniques, as compared with prior art methods, may be utilized for making such devices.

Such devices whose structure is based upon the use of layers of organic optoelectronic materials generally rely on a common mechanism leading to optical emission. Typically, this mechanism is based upon the radiative recombination of a trapped charge. Specifically, OLEDs are comprised of at least two thin organic layers between an anode and a cathode. The material of one of these layers is specifically chosen based on the material's ability to transport holes, a "hole transporting layer" (HTL), and the material of the other layer is specifically selected according to its ability to transport electrons, an "electron transporting layer" (ETL). With such a construction, the device can be viewed as a diode with a forward bias when the potential applied to the anode is higher than the potential applied to the cathode. Under these bias conditions, the anode injects holes (positive charge carriers) into the HTL, while the cathode injects electrons into the ETL. The portion of the luminescent medium adjacent to the anode thus forms a hole injecting and transporting zone while the portion of the luminescent medium adjacent to the cathode forms an electron injecting and transporting zone. The injected holes and electrons each migrate toward the oppositely charged electrode. When an electron and hole localize on the same molecule, a Frenkel exciton is formed. These excitons are trapped in the material which has the lowest energy. Recombination of the short-lived excitons may be visualized as an electron dropping from its conduction potential to a valence band, with relaxation occurring, under certain conditions, preferentially via a photoemissive mechanism.

The materials that function as the ETL or HTL of an OLED may also serve as the medium in which exciton formation and electroluminescent emission occur. Such OLEDs are referred to as having a "single heterostructure" (SH). Alternatively, the electroluminescent material may be present in a separate emissive layer between the HTL and the ETL in what is referred to as a "double heterostructure" (DH).

In a single heterostructure OLED, either holes are injected from the HTL into the ETL where they combine with electrons to form excitons, or electrons are injected from the ETL into the HTL where they combine with holes to form excitons. Because excitons are trapped in the material having the lowest energy gap, and commonly used ETL materials generally have smaller energy gaps than commonly used HTL materials, the emissive layer of a single heterostructure device is typically the ETL. In such an OLED, the materials used for the ETL and HTL should be chosen such that holes can be injected efficiently from the HTL into the ETL. Also, the best OLEDs are believed to have good energy level alignment between the highest occupied molecular orbital (HOMO) levels of the HTL and ETL materials.

In a double heterostructure OLED, holes are injected from the HTL and electrons are injected from the ETL into the separate emissive layer, where the holes and electrons combine to form excitons.

Various compounds have been used as HTL materials or ETL materials. HTL materials mostly consist of triaryl amines in various forms which show high hole mobilities ($\sim 10^{-3}$ cm$^2$/Vs). There is somewhat more variety in the ETLs used in OLEDs. Aluminum tris(8-hydroxyquinolate) (Alq$_3$) is the most common ETL material, and others include oxidiazol, triazol, and triazine.

A well documented cause of OLED failure is thermally induced deformation of the organic layers (e.g. melting, crystal formation, thermal expansion, etc.). This failure mode can be seen in the studies that have been carried out with hole transporting materials, K. Naito and A. Miura, J. Phys. Chem. (1993), 97, 6240–6248; S. Tokito, H. Tanaka, A. Okada and Y. Taga. Appl. Phys. Lett. (1996), 69, (7), 878–880; Y. Shirota, T. Kobata and N. Noma, Chem. Lett. (1989), 1145–1148; T. Noda, I. Imae, N. Noma and Y. Shirota, Adv. Mater. (1997), 9, No. 3; E. Han, L. Do, M. Fujihira, H. Inada and Y. Shirota, J. Appl. Phys. (1996), 80, (6) 3297–701; T. Noda, H. Ogawa, N. Noma and Y. Shirota, Appl. Phys. Lett. (1997), 70, (6), 699–701; S. Van Slyke, C. Chen and C. Tang, Appl. Phys. Lett. (1996), 69, 15, 2160–2162; and U.S. Pat. No. 5,061,569.

Organic materials that are present as a glass, as opposed to a crystalline or polycrystalline form, are desirable for use in the organic layers of an OLED, since glasses are capable of providing higher transparency as well as producing superior overall charge carrier characteristics as compared with the polycrystalline materials that are typically produced when thin films of the crystalline form of the materials are prepared. However, thermally induced deformation of the organic layers may lead to catastrophic and irreversible failure of the OLED if a glassy organic layer is heated above its $T_g$. In addition, thermally induced deformation of a glassy organic layer may occur at temperatures lower than $T_g$, and the rate of such deformation may be dependent on the difference between the temperature at which the deformation occurs and $T_g$. Consequently, the lifetime of an OLED may be dependent on the $T_g$ of the organic layers even if the device is not heated above $T_g$. As a result, there is a need for organic materials having a high $T_g$ that can be used in the organic layers of an OLED.

The most common hole transporting material used in the HTL of OLEDs is a biphenyl bridged diamine, N,N'-diphenyl-N,N'-bis(3-methylphenyl)-1,1-biphenyl-4,4'-diamine (TPD) having the chemical structure:

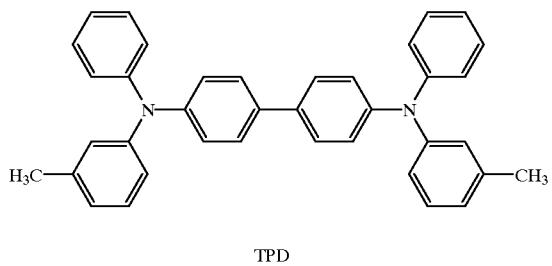

TPD

This material has a good hole mobility and efficiently transfers holes to aluminum tris (8-hydroxyquinoline) in a simple single heterostructure OLED. However, TPD has a melting point of 167° C. and a glass transition temperature of 65° C. If a device prepared with TPD is heated above 65° C., the glass transition temperature, catastrophic and irreversible failure results. In order to increase the glass transition temperature of the HTL, several groups have explored different modifications to the basic structure of TPD, Naito et al.; Tokito et al.; Shirota et al.; Noda et al. (Adv. Mater.); Han et al.; Noda et al. (Appl. Phys. Lett.); Van Slyke et al.; and U.S. Pat. No. 5,061,569. While these studies have led to materials with $T_g$ values as high as 150° C., they have not led to an understanding of why certain structural modifications increase $T_g$, while other modifications may not affect $T_g$ at all or may even lower $T_g$. Still other modifications may produce a material not having a glass transition temperature at all or a material not having the combination of properties that is suitable for use in an HTL. For example, replacing the amine groups of TPD with carbazole groups to produce 4,4'-di(N-carbazolo)diphenyl (CBP), having the chemical structure:

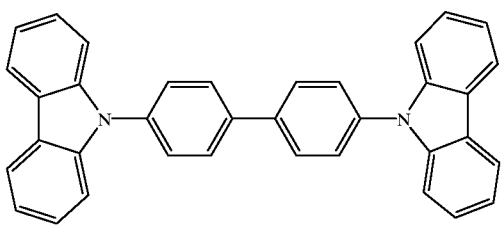

CBP increases the melting point to 285° C. However, the material shows no glass transition. Further changes in the basic structure of TPD can increase the $T_g$ value even higher, but the materials often have poorer hole transporting properties than TPD, i.e. OLEDs made with these high temperature materials give poor device properties in OLEDs compared to TPD.

U.S. Pat. No. 5,061,569 discloses hole transporting materials comprised of at least two tertiary amine moieties and further including an aromatic moiety containing at least two fused aromatic rings attached to the tertiary amine nitrogen atoms. Out of the large number of compounds encompassed by the broadly disclosed class of compounds recited, U.S. Pat. No. 5,061,569 fails to disclose how to select those compounds which have a high glass transition temperature. For example, the naphthyl derivatives do make stable glasses. One such molecule is 4,4'-bis[N-(1-naphthyl)-N-phenyl-amino]biphenyl (α-NPD), having the chemical structure:

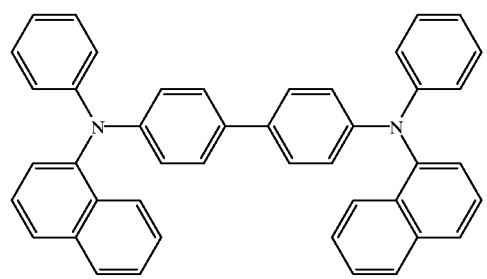

α-NPD

The present inventors' measurements show that α-NPD has a $T_g$ of 100–105° C., which is substantially higher than the $T_g$ of 65° C. of TPD. This material has excellent hole conduction properties, and the $T_g$ of 100–105° C. is higher than the $T_g$ of TPD of about 65° C. OLEDs prepared with NPD have electrical properties very similar to those prepared with TPD. However, 4,4'-bis[N-(2-naphthyl)-N-phenyl-amino]biphenyl (β-NPD), having the structure:

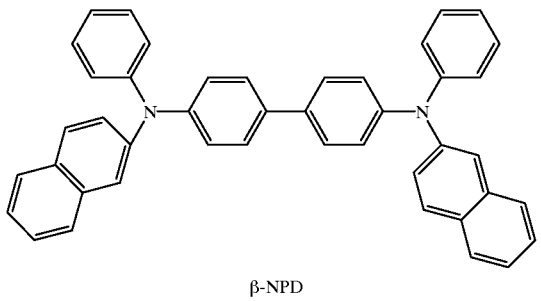

β-NPD has been generally understood to have a $T_g$ which is substantially lower than α-derivative. Apparently because of this purportedly low and anomalous difference between $T_g$ of the α- β-derivatives, there had been no known reports of using the β-derivative as the hole transporting material of an OLED.

It would be desirable if OLED's could be fabricated from glassy charge carrier materials having improved temperature stability, while still providing luminescent characteristics comparable to prior art compounds. As used herein, the term "charge carrier layer" may refer to the hole transporting layer, the electron transporting layer or the separate emissive layer of an OLED having a double heterostructure. In addition, it would be useful to have a method for selecting and preparing such glassy charge carrier materials having improved temperature stability, as characterized, in particular, by glassy charge carrier materials having a high glass transition temperature.

In addition, there is a general inverse correlation between the $T_g$ and the hole transporting properties of a material, i.e., materials having a high $T_g$ generally have poor hole transporting properties. Using an HTL with good hole transporting properties leads to an OLED having desirable properties such as higher quantum efficiency, lower resistance across the OLED, higher power quantum efficiency, and higher luminance. There is therefore a need for a HTL having a high hole mobility and a high glass transition temperature.

SUMMARY OF THE INVENTION

The present invention is directed to organic light emitting devices comprising a heterostructure for producing electroluminescence having a hole transporting layer with a glass structure. The hole transporting layer comprises a compound having a symmetric molecular structure. The end groups of the symmetric molecule are hole transporting amine moieties having an unsaturated linkage between two arenes.

DETAILED DESCRIPTION

Figure 1:
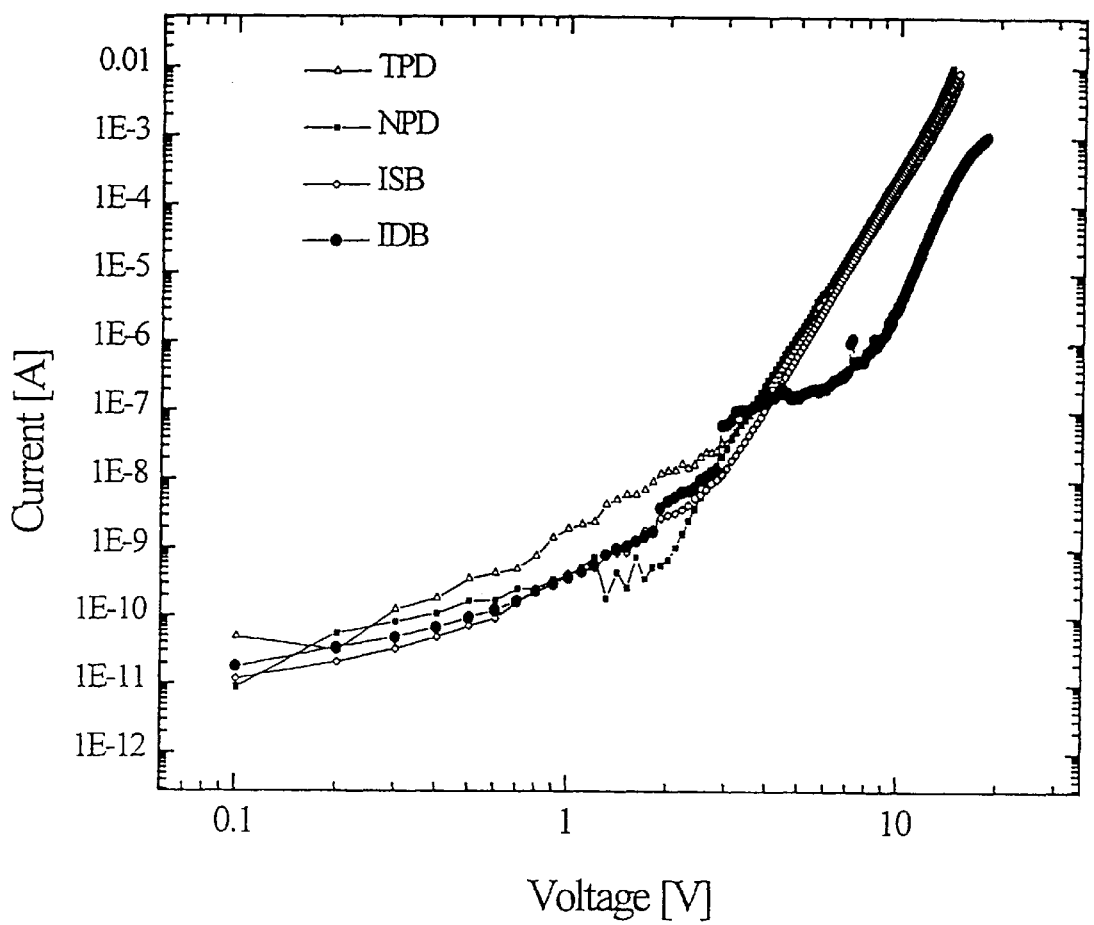
FIG. 1 shows a plot of current v. voltage for an embodiment of the present invention.

The present invention will now be described in detail for specific preferred embodiments of the invention, it being understood that these embodiments are intended only as illustrative examples and the invention is not to be limited thereto.

The present invention is directed to organic light emitting devices comprising a heterostructure for producing electroluminescence having a hole transporting layer with a glass structure. The hole transporting layer comprises a compound having a symmetric molecular structure. The end groups of the symmetric molecule are hole transporting amine moieties having an unsaturated linkage between two arenes.

The term "unsaturated linkage" as used herein refers to a linkage in which there is at least one double bond. The term "arene" as used herein refers to a hydrocarbon containing at least one aromatic. The term "symmetric" as used herein refers to a molecule having a point about which the molecule is symmetric. As used herein, the term "charge carrier layer" may refer to a "hole transporting layer" (HTL,) an "electron transporting layer" (ETL) or, for an OLED having a double heterostructure (DH), a "separate emissive layer."

The term "hole transporting moiety" as used herein, refers to a group which, when present in a material contained in a layer of an OLED, causes the material to provide electrical conduction through the layer, when a voltage is applied, predominantly by the conduction of holes. The term "electron transporting moiety" as used herein, refers to a group which, when present in a material contained in a layer of an OLED, causes the material to provide electrical conduction through the layer, when a voltage is applied, predominantly by the conduction of electrons. The term "hole transporting amine moiety" as used herein, refers to an amine group that is a hole transporting moiety. Such hole transporting amine moieties are typically comprised of nitrogen atoms that are directly bonded to at least two phenyl groups, wherein the two phenyl groups may be joined so as to form a heterocyclic ring including the nitrogen, for example, a carbazole group, or the two phenyl groups may be unattached to each other. Each phenyl group may itself be fused with still another phenyl group, being bonded to the nitrogen atom, for example, either as a 1-naphthyl group or as a 2-naphthyl group.

While not intending to be limited by any particular theory or mechanism for explaining exactly how or why such materials have good hole conducting properties, the inventors' examination of electronic structure by semi-empirical theoretical methods shows that a molecule having end groups that are hole transporting moieties having an unsaturated linkage between two arenes has holes delocalized onto the end groups. One such molecule is 4,4'-(N,N'-bisiminostilbene)biphenyl (ISB). By way of contrast, the normal situation in amines such as TPD and NPD is for the nitrogen lone pair to be conjugated through the biphenyl group, such that the hole is delocalized predominantly onto the biphenyl group. The importance of the unsaturated linkage can be shown by examining 4,4'-(N,N'-iminodibenzyl)biphenyl (IDB), which has the same structure as ISB, except that the IDB has a saturated linkage between the amino phenyl groups, while that of ISB is unsaturated. The inventors analysis shows that IDB has a nitrogen lone pair conjugated through the biphenyl group, whereas ISB has the nitrogen lone pair coupled to the stilbene group, not the biphenyl. To the extent that the hole is delocalized, it is spread onto the stilbene group. This delocalization helps keep the hole on the exterior of the ISB molecule and not on the biphenyl, where it would be shielded from adjacent molecules. Keeping the hole on the exterior of the molecule gives it more contact with adjacent molecules and increases the rate of hole transfer to adjacent molecules, which results in good hole conducting properties.

Moreover, the inventors' analysis shows that substitutions may be made to molecules having end groups that have an unsaturated linkage between two arenes, and the holes would still be delocalized on the ends or periphery of the molecule rather than the center.

In particular, the present invention includes symmetric compounds having a biphenyl bridge, as represented by formula (I):

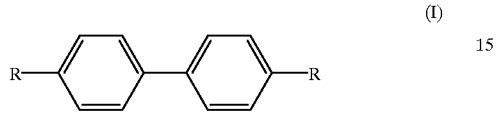

(I)

where R is a hole transporting amine moiety having an unsaturated linkage between two arenes. The molecule represented by formula (I) is symmetric because there is a point in the center of the biphenyl bridge between the two R-groups about which the molecule is symmetric. The term "symmetric" as used herein requires that atoms are on either side of the point of symmetry have the same sequence of bonding between the atoms, i.e., the R-groups must have identical atoms bonded in an identical sequence, but allows for differences in the positions of atoms due to the twisting of bonds.

The present invention also includes symmetric compounds having a phenyl bridge, as represented by formula (II):

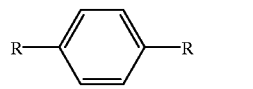

(II)

wherein R has the same meaning as above.

An example of an R-group that is a hole transporting amine moiety having an unsaturated linkage between two arenes is represented by the formula (III):

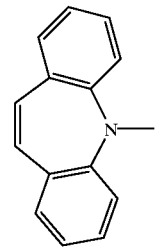

(III)

where the two phenyl groups are the arenes, and the ethenyl group is the unsaturated linkage between the two arenes.

Using the R-group of formula (III) in the molecule of formula (I), the present invention therefore includes ISB, represented by the formula (IV):

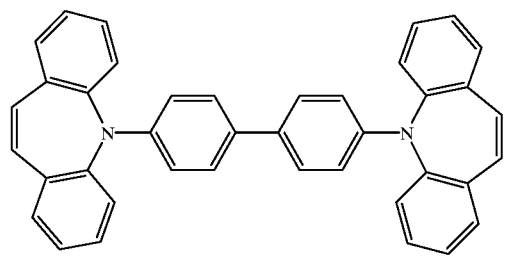

(IV)

ISB

The ethenyl groups of ISB may be substituted while still maintaining the unsaturated linkage between the two arenes. For example, the unsaturated linkage may, in fact, be provided by a phenylene group, resulting in a molecule having a structure as represented by formula (V):

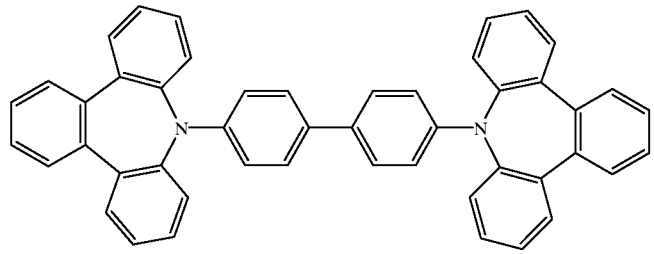

(V)

Alternatively, the ethenyl groups of ISB may be substituted so as to result in a molecule having a structure as represented by formula (VI):

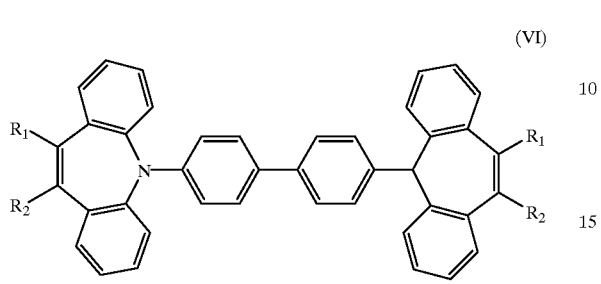

(VI)

where $R_1$ and $R_2$ are selected from the group consisting of: alkyl, phenyl, substituted alkyl, and substituted phenyl groups. $R_1$ may be the same as $R_2$, or may be different.

The substitutions leading to the molecules of formulae (V) and (VI) are expected to assist in shifting the hole delocalization to the ends of the molecule. In addition, the substitutions increase the molecular weight of the molecule and may lead to a higher $T_g$.

In a conventional single heterostructure OLED, the emissive material is the ETL, and the HTL must have an absorption energy higher than that of the ETL. As a result, it is preferable that substitutions made to ISB do not lead to significant shifts in the electronic spectrum if the resultant molecule is to be used in a single heterostructure OLED having an emissive ETL.

To provide a contrast to ISB, a molecule having an R-group that is a hole transporting amine moiety having a saturated linkage between two arenes may be used. Such an R-group is represented by the formula (VII):

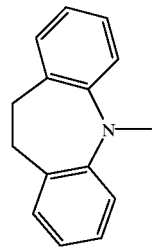

(VII)

Using the R-group of formula (VII) in the molecule of formula (I) results in 4,4'-(N,N'-aminodibenzyl)biphenyl (IDB), as represented by the formula (VIII):

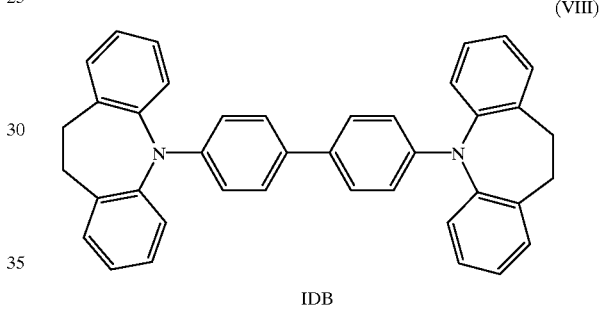

(VIII)

IDB

The thermal and other physical properties of ISB and IDB, as well as those of their phenylene bridged analogs, are given in Table 1:

TABLE 1

Physical data for ISB, IDB and their phenyl bridged analogs.

| compound | melting point (° C.) | $T_g$ (° C.) | $\lambda_{max}$ abs. (nm) | $\lambda_{max}$ PL (nm) |
| --- | --- | --- | --- | --- |
| ISB | 317 | 110 | 300, 340 | 530 |
| IDB | — | 117 | 320 | 402 |
| | — | 73 | 315 | 368 |

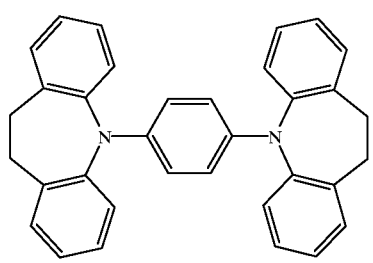

TABLE 1-continued

Physical data for ISB, IDB and their phenyl bridged analogs.

| compound | melting point (° C.) | T$_g$ (° C.) | λ$_{max}$ abs. (nm) | λ$_{max}$ PL (nm) |
|---|---|---|---|---|
| | 310 | 110 | 290, 340 | 444, 488 |

The T$_g$ of both ISB (110° C.) and IDB (117° C.) are significantly higher than that of HTL materials conventionally used in OLEDs, such as TPD (65° C.) and NPD (105° C.), which are materials conventionally used in OLEDs. As a result, OLEDs using ISB or IDB as an HTL may be operated at a higher temperature than OLEDs using TPD or NPD, and are expected to have a longer lifetime when operated at the same temperature.

As discussed in greater detail below, two different types of OLEDS were fabricated using ISB and IDB as HTL materials. Similar OLEDs were also fabricated using TPD and NPD as HTL materials. Both types of OLED start with an ITO coated substrate as an anode and use a Mg—Ag cathode. The simplest OLED structure examined was ITO/HTL/Alq$_3$/Mg—Ag. A slightly more complicated structure uses a copper phthalocyanine, CuPc, hole injector, i.e. ITO/CuPc/HTL/Alq$_3$/Mg—Ag. The use of a CuPc hole injector, such as disclosed in copending application Ser. No. 08/865,491, can provide improved quantum yields. As illustrated in Table 2, it was observed for both types of OLED that OLEDS using ISB as the HTL have superior performance to those using IDB, and that OLEDs using ISB have performance comparable to that of OLEDs using NPD:

as the HTL in several respects. The ISB based OLEDs have a higher quantum efficiency, a require a lower voltage to achieve the same current, and have a higher luminance at the same current. ISB and IDB are both symmetric molecules having a high T$_g$. The only structural difference between ISB and IDB is that ISB has an unsaturated linkage between the amino phenyl groups, while that of IDB is saturated. This difference in the properties of OLEDs using ISB as opposed to IDB is consistent with ISB having better hole conducting properties than IDB. While the T$_g$ of IDB is slightly higher than that of ISB, this higher T$_g$ alone is not expected to alter the OLED properties by the amount observed here.

The OLEDs of the present invention are comprised of a heterostructure for producing electroluminescence which may be fabricated as a single heterostructure or as a double heterostructure. As used herein, the term "heterostructure for producing electroluminescence" refers to a heterostructure that includes for a single heterostructure, for example, a substrate, a hole injecting anode layer in contact with the substrate, a HTL in contact with the anode layer, an ETL in contact with the HTL, and an electrode injecting cathode layer in contact with the ETL. If the cathode layer is a metal cathode layer of Mg:Ag, then a metal protective layer, for

TABLE 2

| | Quantum Efficiency with CuPc layer | Quantum Efficiency without CuPc layer | V @ 0.1 mA with CuPc layer | V @ 0.1 mA without CuPc layer | Power Q.E. with CuPc layer at 200 cd/m$^2$ (W/W) | Power Q.E. without CuPc layer at 200 cd/m$^2$ (W/W) | Luminance @ 5 mA for 1 mm dot with CuPc layer | Luminance @ 5 mA for mm dot without CuPc layer |
|---|---|---|---|---|---|---|---|---|
| ISB | 0.58% | 0.62% | 7.5 V | 9.0 V | 0.174 | 0.156 | 8460 | 8930 |
| IDB | 0.30% | 0.15% | 9.5 V | 12.9 V | 0.071 | 0.025 | 1510 @ 1 mA | 470 @ 1 mA |
| α-NPD | 0.85% | 0.88% | 7.3 V | 8.65 V | 0.285 | 0.251 | 12550 | 12925 |
| TPD | 0.78% | 0.93% | 8.25 V | 9.20 V | 0.230 | 0.250 | 11280 | 13865 |

The quantum yields, turn-on voltages and power efficiencies of the ISB based devices are very good and the higher T$_g$ suggests that the ISB based OLEDs would have significantly improved lifetime, and can be operated at higher temperatures, than NPD and TPD based OLEDs. The similarity of the TPD, NPD and ISB OLED device properties can also be seen in FIGS. 1 and 2. The current-voltage plots of OLEDs made TPD, NPD and ISB are nearly indistinguishable, while IDB is poorer.

Table 2 also shows that OLEDs using ISB as the HTL have significantly better properties than OLEDs using IDB example, made of a layer of Ag for protecting the Mg:Ag cathode layer from atmospheric oxidation, may also be present.

The heterostructure for producing electroluminescence may also include a protection layer and/or an injection enhancement layer between the anode layer and the HTL or the cathode layer and the ETL. The protection layer serves to protect the underlying organic layers from damage during deposition of an ITO layer, for example. An injection enhancement layer serves to enhance injection of holes from the anode into the adjacent HTL, such as disclosed in copending Ser. No. 08/865,491, for example, or to enhance injection of electrons from the cathode into the adjacent ETL, such as disclosed in copending application Ser. No. 08/964,863, and copending application entitled "Highly Transparent Non-Metallic Cathodes," attorney docket no. 10020/65 (filed Apr. 3, 1998), for example.

If a double heterostructure is used to produce electroluminescence, a separate emissive layer is included between the HTL and the ETL. The term "emissive layer" as used herein may refer either to the emissive electron transporting layer or emissive hole transporting layer of a single heterostructure or the separate emissive layer of a double heterostructure. The emissive layer of a double heterostructure is referred to as a "separate" emissive layer so as to distinguish it from the ETL of a single heterostructure, which may also be an emissive layer. The materials, methods and apparatus for preparing the organic thin films of a single or double heterostructure are disclosed, for example, in U.S. Pat. No. 5,554,220, which is incorporated herein in its entirety by reference.

Alternatively, the heterostructure for producing electroluminescence may have an inverted (IOLED) structure in which the sequence of layers deposited on the substrate is inverted, that is, an electron injecting cathode layer is in direct contact with the substrate, an electron transporting layer is in contact with the cathode layer, a hole transporting layer is in contact with the electron transporting layer, and a hole injecting anode layer is in contact with the hole transporting layer.

If the heterostructure for producing electroluminescence is included as part of a stacked OLED (SOLED), one or both of the electrodes of an individual heterostructure may be in contact with an electrode of an adjacent heterostructure. Alternatively, dependent on the circuitry used to drive the SOLED, an insulating layer may be provided between adjacent electrodes of two of the OLEDs in the stack.

The single or double heterostructures as referred to herein are intended solely as examples for showing how an OLED embodying the present invention may be fabricated without in any way intending the invention to be limited to the particular materials or sequence for making the layers shown. For example, a single heterostructure typically includes a substrate which may be opaque or transparent, rigid or flexible, and/or plastic, metal or glass; a first electrode, which is typically a high work function, hole-injecting anode layer, for example, an indium tin oxide (ITO) anode layer; a hole transporting layer; an electron transporting layer; and a second electrode layer, for example, a low work function, electron-injecting, metal cathode layer of a magnesium-silver alloy, (Mg:Ag) or of a lithium-aluminum alloy, (Li:Al).

Materials that may be used as the substrate in a representative embodiment of the present invention include, in particular, glass, transparent polymer such as polyester, sapphire or quartz, or substantially any other material that may be used as the substrate of an OLED.

Materials that may be used as the hole-injecting anode layer in a representative embodiment of the present invention include, in particular, ITO, Zn—In—$SnO_2$ or $SbO_2$, or substantially any other material that may be used as the hole-injecting anode layer of an OLED.

In addition to the materials as disclosed herein for use in the HTL or in the ETL, other materials that may be used in the HTL in a representative embodiment of the present invention include, in particular, N,N'-diphenyl-N,N'-bis(3-methylphenyl)1-1'biphenyl-4,4'diamine (TPD), 4,4'-bis[N-(1-naphthyl)-N-phenyl-amino]biphenyl (α-NPD) or 4,4'-bis [N-(2-naphthyl)-N-phenyl-amino]biphenyl (β-NPD). Other materials that may be used as the ETL include, in particular, aluminum tris(8-hydroxyquinolate) ($Alq_3$), a carbazole, an oxadiazole, a triazole, a thiophene or oligothiophene group. Other materials that may be used as the separate emissive layer, if present, include, in particular, dye-doped $Alq_3$, or substantially any other material that may be used as the separate emissive layer of an OLED.

Materials that may be used as the electron-injecting, metal cathode layer in a representative embodiment of the present invention include, in particular, Mg—Ag, Li—Ag or Ca, or a non-metallic material such as ITO, such as disclosed in copending Ser. No. 08/964,863, or substantially any other material that may be used as the cathode layer of an OLED.

The insulating layer, if present, may be comprised of an insulating material such as $SiO_2$, $SiN_x$ or $AlO_2$, or substantially any other material that may be used as the insulating material of an OLED, which may be deposited by a variety of processes such as plasma enhanced chemical vapor deposition (PECVD), electron beam, etc.

The OLEDs of the present invention have the advantage that they can be fabricated entirely from vacuum-deposited molecular organic materials as distinct, for example, from OLEDs in which some of the layers are comprised of polymeric materials, which cannot be readily deposited using vacuum deposition techniques. A vacuum-deposited material is one which can be deposited in a vacuum typically having a background pressure less than one atmosphere, preferably about $10^{-5}$ to about $10^{-11}$ torr for vacuum deposition, or about 50 torr to about $10^{-5}$ torr for vapor deposition.

Although not limited to the thickness ranges recited herein, the substrate may be as thin as $10\mu$, if present as a flexible plastic or metal foil substrate, such as aluminum foil, or substantially thicker if present as a rigid, transparent or opaque, substrate or if the substrate is comprised of a silicon-based display driver; the ITO anode layer may be from about 500 Å (1 Å=$10^-$cm) to greater than about 4000 Å thick; the hole transporting layer from about 50 Å to greater than about 1000 Å thick; the separate emissive layer of a double heterostructure, if present, from about 50 Å to about 200 Å thick; the electron transporting layer from about 50 Å to about 1000 Å thick; and the metal cathode layer from about 50 Å to greater than about 100 Å thick, or substantially thicker if the cathode layer includes a protective silver layer and is opaque.

Thus, while there may be substantial variation in the type, number, thickness and order of the layers that are present, dependent on whether the device includes a single heterostructure or a double heterostructure, whether the device is a SOLED or a single OLED, whether the device is a TOLED or an IOLED, whether the OLED is intended to produce emission in a preferred spectral region, or whether still other design variations are used, the present invention is directed to those devices in which the OLED comprises a heterostructure for producing electroluminescence having a hole transporting layer with a glass structure, where the hole transporting layer comprises a compound having a symmetric molecular structure, and the end groups of the symmetric molecule are hole transporting amine moieties having an unsaturated linkage between two arenes. The compound may be substantially the only component of the hole transporting layer, may be the predominant component in a hole transporting layer that is doped with other materials, or may be a dopant in the hole transporting layer. The hole transporting layer may be emissive, for example in a single heterostructure OLED having an emissive hole transporting layer, or may be non-emissive.

The subject invention as disclosed herein may be used in conjunction with co-pending applications: "High Reliability, High Efficiency, Integratable Organic Light Emitting Devices and Methods of Producing Same", Ser. No. 08/774,119 (filed Dec. 23, 1996); "Novel Materials for Multicolor LED's", Ser. No. 08/850,264 (filed May 2, 1997); "Electron Transporting and Light Emitting Layers Based on Organic Free Radicals", Ser. No. 08/774,120 (filed Dec. 23, 1996); "Multicolor Display Devices", Ser. No. 08/772,333 (filed Dec. 23, 1996); "Red-Emitting Organic Light Emitting Devices (LED's)", Ser. No. 08/774,087 (filed Dec. 23, 1996); "Driving Circuit For Stacked Organic Light Emitting Devices", Ser. No. 08/792,050 (filed Feb. 3, 1997); "High Efficiency Organic Light Emitting Device Structures", Ser. No. 08/772,332 (filed Dec. 23, 1996); "Vacuum Deposited, Non-Polymeric Flexible Organic Light Emitting Devices", Ser. No. 08/789,319 (filed Jan. 23, 1997); "Displays Having Mesa Pixel Configuration", Ser. No. 08/794,595 (filed Feb. 3, 1997); "Stacked Organic Light Emitting Devices", Ser. No. 08/792,046 (filed Feb. 3, 1997); "High Contrast Transparent Organic Light Emitting Device Display", Ser. No. 08/821,380 (filed Mar. 20, 1997); "Organic Light Emitting Devices Containing A Metal Complex of 5-Hydroxy-Quinoxaline as A Host Material", Ser. No. 08/838,099 (filed Apr. 15, 1997); "Light Emitting Devices Having High Brightness", Ser. No. 08/844,353 (filed Apr. 18, 1997); "Organic Semiconductor Laser", Ser. No. 60/046,061 (filed May 9, 1997); "Organic Semiconductor Laser", Ser. No. 08/859,468 (filed May 19, 1997); "Saturated Full Color Stacked Organic Light Emitting Devices", Ser. No. 08/858,994 (filed May 20, 1997); "An Organic Light Emitting Device Containing a Hole Injection Enhancement Layer", Ser. No. 08/865,491 (filed May 29, 1997); "Plasma Treatment of Conductive Layers", Ser. No. PCT/US97/10252; (filed Jun. 12, 1997); "Patterning of Thin Films for the Fabrication of Organic Multi-Color Displays", Ser. No. PCT/US97/10289 (filed Jun. 12, 1997); "Double Heterostructure Infrared and Vertical Cavity Surface Emitting Organic Lasers", Ser. No. 60/053,176 (filed Jul. 18, 1997); "Oleds Containing Thermally Stable Asymmetric Charge Carrier Materials", Ser. No. 08/929,029 filed (Sep. 8, 1997), "Light Emitting Device with Stack of Oleds and Phosphor Downconverter", Ser. No. 08/925,403 (filed Sep. 9, 1997), "An Improved Method for Depositing Indium Tin Oxide Layers in Organic Light Emitting Devices", Ser. No. 08/928,800 (filed Sep. 12, 1997), "Azlactone-Related Dopants in the Emissive Layer of an Oled" (filed Oct. 9, 1997), Ser. No. 08/948,130, "A Highly Transparent Organic Light Emitting Device Employing A Non-Metallic Cathode", (filed Nov. 3, 1997), Ser. No. 08/064,005 (Provisional), "A Highly Transparent Organic Light Emitting Device Employing a Non-Metallic Cathode", (filed Nov. 5, 1997), Ser. No. 08/964,863, "Low Pressure Vapor Phase Deposition of Organic Thin Films" (filed Nov. 17, 1997), Ser. No. 08/972,156, "Method of Fabricating and Patterning Oleds", (filed Nov. 24, 1997), Ser. No. 08/977,205, "Method for Deposition and Patterning of Organic Thin Film", (filed Nov. 24, 1997), Ser. No. 08/976,666, "Oleds Doped with Phosphorescent Compounds", (filed Dec. 1, 1997), Ser. No. 08/980,986, "Organic Vertical-Cavity Surface-Emitting Laser Confirmation", (filed Jan 22, 1998), Ser. No. 09/010,594; "Electron Transporting and Light Emitting Layers Based on Organic Free Radicals", (filed Feb. 18, 1998), Ser. No. 09/025,660; "Method of Making a Display", (filed Mar. 30, 1998), Ser. No. 09/050,084; "Aluminum Complexes Bearing Both Electron Transporting and Hole Transporting Moieties" (filed Apr. 1, 1998), Attorney Docket No. 10020/66; "Highly Transparent Non-Metallic Cathodes" (filed Apr. 3, 1998), Attorney Docket No. 10020/65; and "Color-Tunable Organic Light Emitting Devices" (filed Apr. 10, 1998), Attorney Docket No. 10020/60, each co-pending application being incorporated herein by reference in its entirety. The subject invention may also be used in conjunction with the subject matter of each of co-pending U.S. patent application Ser. Nos. 08/354,674, 08/613,207, 08/632,322 and 08/693,359 and provisional patent application Ser. Nos. 60/010,013, 60/024,001 and 60/025,501, each of which is also incorporated herein by reference in its entirety.

OLEDs of the present invention may be fabricated using the materials and structures as disclosed in these co-pending applications.

It has been shown in co-pending application "Oleds Containing Thermally Stable Asymmetric Charge Carrier Materials", Ser. No. 08/929,029 (filed Sep. 8, 1997), which is incorporated herein by reference in its entirety, that charge carrier materials having an asymmetric molecular structure may have a high $T_g$ and be suitable for use in an OLED. It has also been shown in that application that β-NPD may be suitable for use as a charge carrier material in an OLED. OLEDs of the present invention may be fabricated using the materials and structures as disclosed in this co-pending application.

The OLED of the present invention may be used in substantially any type of device which is comprised of an OLED, for example, in OLEDs that are incorporated into a larger display, a vehicle, a computer, a television, a printer, a large area wall, theater or stadium screen, a billboard or a sign.

This invention will now be described in detail with respect to showing how certain specific representative embodiments thereof can be made, the materials, apparatus and process steps being understood as examples that are intended to be illustrative only. In particular, the invention is not intended to be limited to the methods, materials, conditions, process parameters, apparatus and the like specifically recited herein.

Procedures for Fabrication of Organic Light-Emitting Devices (OLEDs):

Chemicals:

ISB was prepared according to the following procedure: A round bottom flask was charged with Na-t-butoxide (4.25 g), $Pd_2dba_3$ (0.22 g), DPPF (diphenylphosphinoferrocene 0.33 g), and 50 ml anhydrous toluene. The reaction mixture was stirred under argon at 90° C. for 15 minutes. Then dibromobiphenyl (3.12 g) and iminostilbene (4.25 g) were added, and the reaction was stirred for 8 hours until the amine could not be detected by mass spectroscopy. The solvent was then stripped from the reaction mixture and the crude residue was dried under vacuum. The dried residue was then subjected to a gradient sublimation under reduced pressure ($10^{-4}$ torr). The sublimation yielded 2.06 g of pure material, 36% of the theoretical reaction yield.

IDB was prepared according to the following procedure: 51 mmol (10.000 g) iminodibenzyl was reacted with 17 mmol (6.94 g) 4,4'-diiodobiphenyl. The reaction product was added to a round bottom flask fitted with a condenser, along with 34 mmol (2.16 g) copper powder, 68 mmol (9.398 g) potassium carbonate, 2 mmol (0.530 g) 18-crown-6 ether, and 20 ml o-dichlorobenzene. The flask was heated to 185° C. and then refluxed under argon for 24 hours. The reaction mixture was filtered hot and the filtrate was put under vacuum to remove the solvent. The residue was then passed through a short column of silica gel in toluene. The solvent was then removed from the column filtrate and the solid left behind was sublimed at 220° C. under a vacuum of 0.01 Torr. for purification.

The electron transporting material $Alq_3$, as well as the TPD and NPD, were synthesized according to literature procedure. All organic materials were sublimed before use. Procedures:

ITO/Borosilicate substrates (100 Ω/square) were cleaned by sonicating with detergent for five minutes followed by rinsing with deionized water. They were then treated twice in boiling 1,1,1 -trichloroethane for two minutes. The substrates were then sonicated twice with acetone for two minutes and twice with methanol for two minutes.

The background pressure prior to deposition was $8 \times 10^{-7}$ torr and the pressure during the deposition was around $5 \times 10^{-7}$ to $2 \times 10^{-6}$ torr.

The chemicals were sublimed from resistively heated tantalum boats, and then deposited at a rate from 1 to 3.6 Å/s. The thickness was controlled at 300 Å.

The electron transporting layer ($Alq_3$) was deposited at a rate between 1 to 3.3 Å/s. The total thickness of this layer was controlled at 450 Å.

The substrates were then released to air and masks were put directly on the substrates. The masks are made of stainless steel sheet and contain holes with diameters of 0.25, 0.5, 0.75, and 1.0 mm. The substrates were then put back into vacuum for further coating.

Magnesium and silver were co-deposited at a rate of 2 Å/s. The ratio of Mg:Ag was 9:1. The thickness of this layer was 500 Å. Finally, 1000 Å Ag was deposited at the rate of 2.7 Å/s.

Characteristics of the Devices:

The devices were characterized within one day of fabrication. I-V curves, quantum yields, and luminance were measured. OLED data derived from these measured quantities are tabulated in Table 2. The current-voltage (I—V) characteristics for the devices are shown in FIGS. 1 and 2.

FIG. 1 shows the current-voltage characteristics of OLEDs having a single heterostructure comprising: an ITO anode, an HTL, an $Alq_3$ ETL, and an Mg—Ag cathode, deposited sequentially on a substrate, as discussed above. Four different plots are shown for four different HTL materials: TPD, NPD, ISB and IDB. The current-voltage plots for TPD, NPD and ISB are very similar, showing that the current-voltage characteristics of the OLED do not significantly change, regardless of whether the HTL is TPD, NPD or ISB. The current-voltage plot for IDB shows a lower current than the plots for TPD, NPD and ISB, indicating that IDB may be a less desirable HTL from the perspective of current-voltage characteristics.

Figure 2:
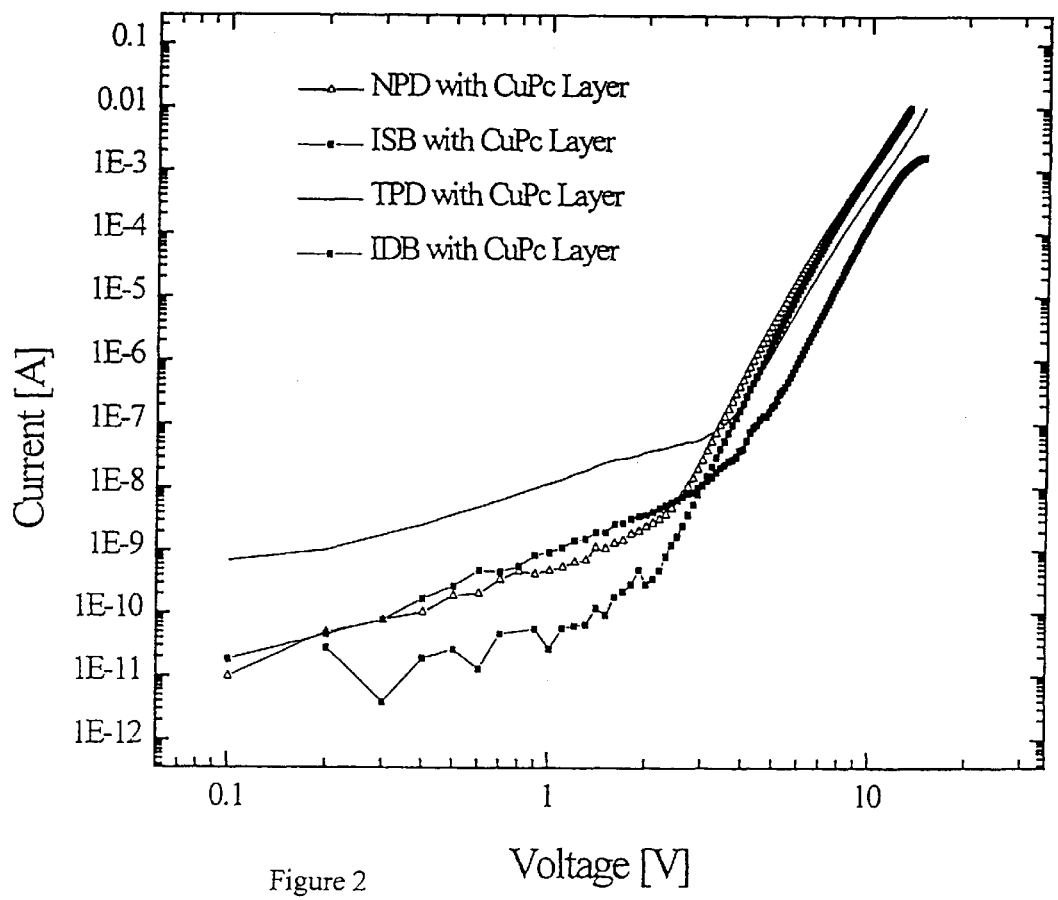
FIG. 2 shows a plot of current v. voltage for an embodiment of the present invention having a CuPc hole injection enhancement layer.

FIG. 2 shows the current-voltage characteristics of OLEDs having a single heterostructure with a hole injection enhancement layer, comprising: an ITO anode, a CuPc hole injection enhancement layer, an HTL, an $Alq_3$ ETL, and an Mg—Ag cathode, deposited sequentially on a substrate, as discussed above. Four different plots are shown for four different HTL materials: TPD, NPD, ISB and IDB. The current-voltage plots for TDP, NPD and ISB are very similar, showing that the current-voltage characteristics of the OLED do not significantly change, regardless of whether the HTL is TPD, NPD or ISB. The current-voltage plot for IDB shows a lower current than the plots for TPD, NPD and ISB, indicating that IDB may be a less desirable HTL from the perspective of current-voltage characteristics.

FIGS. 1 and 2 show that OLEDs using ISB as the HTL can have current-voltage characteristics similar to those of OLEDs using TPD or NPD as the HTL, for two different OLED configurations. This similarity, in conjunction with the higher $T_g$ of ISB and the longer expected lifetimes of OLEDs using ISB, indicate that ISB is a superior HTL.

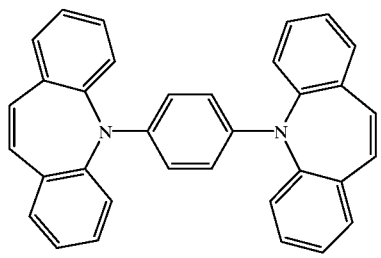

What is claimed is:

1. An organic light emitting device comprising a heterostructure for producing electroluminescence, wherein the heterostructure comprises a hole transporting layer having a glass structure, and wherein the hole transporting layer comprises a compound having the formula:

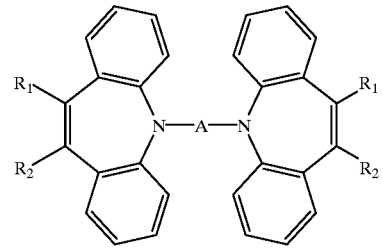

wherein A consists of one or two phenyl groups and $R_1$ and $R_2$ are, independently of one another, selected from the group consisting of hydrogen, an alkyl group, a phenyl group, a substituted alkyl group and a substituted phenyl group, and wherein $R_1$ and $R_2$ may be bridged.

2. The organic light emitting device of claim 1, wherein the compound has the formula:

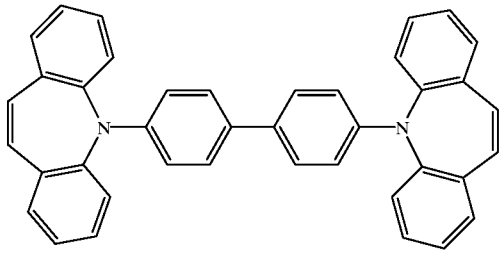

3. The organic light emitting device of claim 1, wherein the compound has the formula:

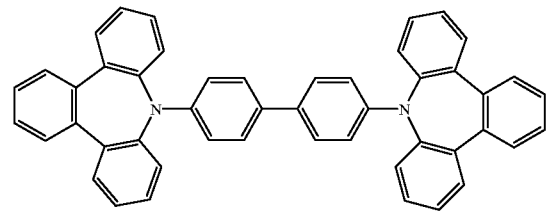

4. The organic light emitting device of claim 1, wherein the compound has the formula:

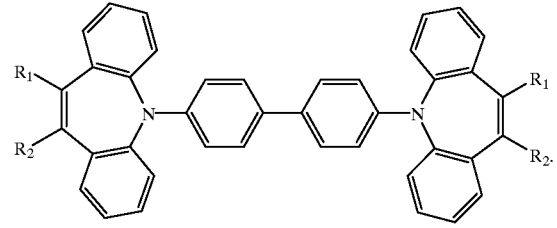

5. The organic light emitting device of claim 1, wherein $R_1$ and $R_2$ are the same.

6. The organic light emitting device of claim 1, wherein $R_1$ and $R_2$ are different.

7. The organic light emitting device of claim 1, wherein the compound has the formula:

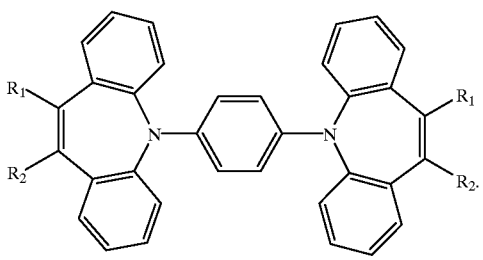

8. The organic light emitting device of claim 1, wherein the compound is the predominant component in the hole transporting layer.

9. The organic light emitting device of claim 1, wherein the compound is present as a dopant in the hole transporting layer.

10. The organic light emitting device of claim 1 wherein the heterostructure for producing electroluminescense comprises, in sequence, a substrate, a cathode layer, an electron transporting layer, the hole transporting layer and an anode layer.

11. The organic light emitting device of claim 1 wherein the heterostructure for producing electroluminescense comprises, in sequence, a substrate, a cathode layer, an electron transporting layer, the hole transporting layer, a hole injector layer and an anode layer.

12. The organic light emitting device of claim 1 wherein the heterostructure for producing electroluminescense comprises, in sequence, a substrate, a cathode layer, an electron transporting layer, an emissive layer, the hole transporting layer and an anode layer.

13. The organic light emitting device of claim 1 wherein the heterostructure for producing electroluminescense comprises, in sequence, a substrate, a cathode layer, an electron transporting layer, the hole transporting layer, an emissive layer, a hole injector layer and an anode layer.

14. The organic light emitting device of claim 1 wherein the heterostructure for producing electroluminescense comprises, in sequence, a substrate, an anode layer, the hole transporting layer, an electron transporting layer, and a cathode layer.

15. The device of claim 1, wherein the device is incorporated into a display.

16. The device of claim 1, wherein the device is incorporated into a vehicle.

17. The device of claim 1, wherein the device is incorporated into a computer.

18. The device of claim 1, wherein the device is incorporated into a television.

19. The device of claim 1, wherein the device is incorporated into a printer.

20. The device of claim 1, wherein the device is incorporated into a wall, theater or stadium screen.

21. The device of claim 1, wherein the device is incorporated into a billboard or a sign.

22. The organic light emitting device of claim 1 wherein said compound has the formula: